United States Patent [19]

Robin et al.

[11] Patent Number: 5,119,831
[45] Date of Patent: Jun. 9, 1992

[54] SYSTEM AND METHOD FOR DETECTING PRESSURE OF SELECTED BODY PARTS

[75] Inventors: Donald A. Robin, Coralville; Erich S. Luschei, Iowa City, both of Iowa

[73] Assignee: University of Iowa Research Foundation, Oakdale, Iowa

[21] Appl. No.: 640,281

[22] Filed: Jan. 11, 1991

[51] Int. Cl.⁵ ............................................. A61B 5/103
[52] U.S. Cl. ...................................... 128/774; 73/379
[58] Field of Search ......................... 128/26, 774–782; 606/192, 197; 73/862.53, 865.4, 379

[56] References Cited

U.S. PATENT DOCUMENTS

| D. 274,260 | 6/1984 | Wiedel | D24/19 |
|---|---|---|---|
| 3,401,685 | 9/1968 | Staub | 128/24 |
| 3,508,000 | 4/1970 | Snyder | 179/1 |
| 3,556,093 | 1/1971 | Quick | 128/137 |
| 3,867,770 | 2/1975 | Davis | 128/DIG. 29 |
| 4,073,071 | 2/1978 | Angelotti | 35/35 R |
| 4,087,632 | 5/1978 | Hafer | 179/15 D |
| 4,112,596 | 9/1978 | Fletcher et al. | 128/25 |
| 4,175,338 | 11/1979 | Takinishi et al. | 35/17 |
| 4,231,255 | 11/1980 | Haski et al. | 128/774 |
| 4,232,687 | 11/1980 | Anderson-Shanklin | 128/777 |
| 4,310,002 | 1/1982 | Takinishi et al. | 128/642 |
| 4,334,542 | 6/1982 | Takinishi et al. | 128/642 |
| 4,402,327 | 9/1983 | Lambert et al. | 128/774 |
| 4,460,342 | 7/1984 | Mills | 434/185 |
| 4,473,905 | 9/1984 | Katz et al. | 381/70 |
| 4,502,150 | 2/1985 | Katz et al. | 381/70 |
| 4,550,427 | 10/1985 | Katz et al. | 381/70 |
| 4,593,689 | 6/1986 | White | 128/201.19 |
| 4,627,095 | 12/1986 | Thompson | 381/70 |
| 4,672,673 | 6/1987 | Katz et al. | 381/70 |
| 4,697,601 | 10/1987 | Durkee et al. | 128/777 |
| 4,774,945 | 10/1988 | White et al. | 128/207.18 |
| 4,776,347 | 10/1988 | Matthews | 128/774 |
| 4,949,729 | 8/1990 | Haski | 128/774 |

OTHER PUBLICATIONS

Ray D. Kent et al., "Maximum Performance Tests of Speech Production", *Journal of Speech and Hearing Disorders*, vol. 52, 367–387, Nov., 1987.

Theodore L. Munsat, M.D., Ed., *Quantification of Neurologic Deficit*, copyrighted 1989 by Butterworth Publishers, div. of Reed (U.S.A.), Chaps. 7 and 8 entitled, "Measurement of Strength in Neuromuscular Diseases" and Clinical Measurements of Fatigue and Exercise in Neuromuscular Disease, respectively.

Martin F. Palmer, Sc.D. et al., "A Study of Tongue Pressures of Speech Defective and Normal Speaking Individuals", *Journal of Speech Disorders*, vol. 5, 133–140, 1946.

Primary Examiner—Max Hindenburg
Attorney, Agent, or Firm—Dann, Dorfman, Herrell and Skillman

[57] ABSTRACT

A portable pressure detecting device is provided employing a fluid-filled bulb of a suitable size to fit within the mouth of a person to sense pressure generated within the mouth. In addition, a fluid-filled bulb of a suitable size to fit within the hand of the person serves to sense pressure generated by the hand. A transducer is alternatively connectable with each bulb for converting the pressure sensed by the connected bulb to an electrical signal representing the sensed pressure. A pressure comparator circuit is responsive to the electrical signal for comparing the sensed pressure to a selected predetermined pressure level for producing an output indicating the proportion of the sensed pressure relative to the predetermined pressure level. A peak pressure detection circuit is responsive to the electrical signal for detecting the peak pressure sensed by the bulb. An LCD display selectively displays the sensed moment-to-moment pressure, the peak pressure, or the selected predetermined pressure level. An LED display selectively displays the proportion of the sensed pressure relative to the predetermined pressure level.

41 Claims, 4 Drawing Sheets

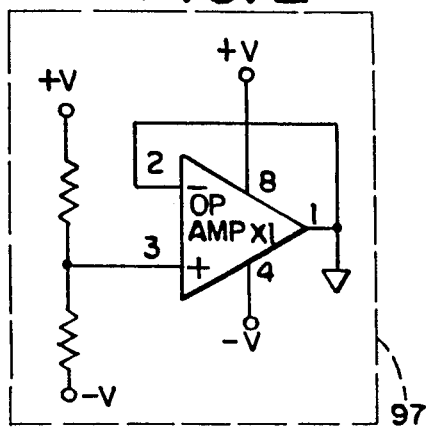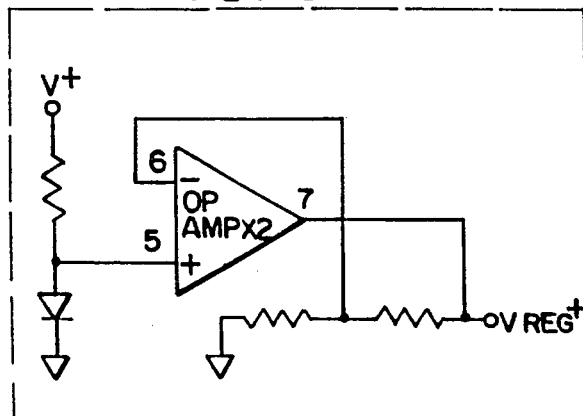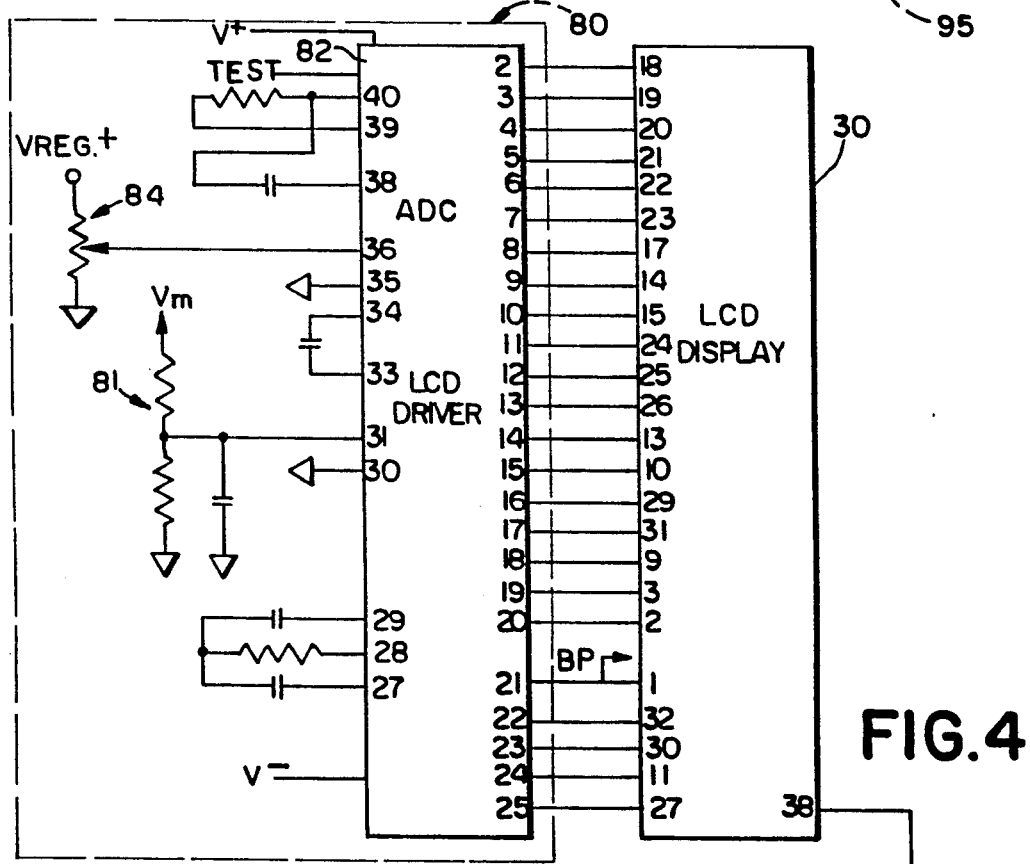

SYSTEM AND METHOD FOR DETECTING PRESSURE OF SELECTED BODY PARTS

FIELD OF THE INVENTION

The present invention relates to a system and method for detecting pressure generated by selected parts of the body of a person, such as the mouth and hand, for aid in the diagnosis of various speech disorders and pathological conditions. More particularly, the invention relates to a portable, battery-powered device for accurately monitoring pressure generated within the mouth of a person by tongue exertion or sucking and for an associated use in detecting the pressure generated by the squeeze of the person's hand for the purpose of aiding in the evaluation and diagnosis of various speech disorders and pathological conditions affecting speech.

BACKGROUND OF THE INVENTION

Information about the structure and function of the oral mechanism is believed to be useful in gaining an in-depth understanding of various factors that contribute to a speech production impairment. Clinical evaluations of speech disorders are frequently made by speech professionals, such as clinicians and speech-language pathologists, based upon findings from an oral mechanism examination of the patient. During the examination, various information concerning the performance of the articulators of the patient is collected.

One measure frequently obtained by clinicians during an oral mechanism examination is the strength of the articulatory muscles, particularly the tongue. One of the problems, however, in obtaining reliable tongue strength information is that most strength measurements are made subjectively by the clinician. For example, the patient is frequently asked to press the tongue as hard as possible against a tongue blade. Judgments are then made by the clinician as to the strength of the tongue. Subjective judgments of tongue strength, however, may not always provide consistent or reliable results. For example, subtle weaknesses of the tongue may not be consistently detected, or even detected at all, by subjective tongue strength measurements. In addition, small incremental decreases or increases in tongue strength related to either disease progression or therapy are also sometimes difficult to detect by subjective measures.

Another potential deficiency with routine oral mechanism examinations is that measurements of tongue endurance or fatigability are not generally made. In addition to tongue strength, tongue endurance or fatigue may be an important factor to assess in diagnosing various speech problems or pathological conditions affecting the oral mechanism. For example, rapid fatigue may result in the inability of the patient to maintain accurate articulatory postures during continuous speech. Moreover, changes in fatigue measurements during periodic reassessments may also aid in the evaluation of the progression of a particular disease or the benefit derived from a selected treatment program.

While some instrumentation has been developed to aid in the detection of tongue strength, certain drawbacks still exist. For example, a force transduction system has been employed in which subjects press their tongues against a metal lever to detect the force that can be generated by the tongue. A potential drawback, however, is that the use of the rigid lever may cause patient discomfort thereby adversely affecting a patient's willingness, if not ability, to exert maximum force on the lever with the tongue.

Still other conventional systems have been developed in which a thick-walled, hollow rubber ball is employed in conjunction with a mercury-filled manometer to measure pressure generated by the tongue. This type of system also suffers from drawbacks. For example, the use of a relatively hard rubber ball may not always be suitable to detect relatively small applications of pressure. In addition, the use of a mercury-filled manometer may not be convenient. For example, the system lacks the capability to provide consistent steady readings as well as a convenient output for conducting tongue endurance and fatigability tests.

In accordance with the present invention, a highly efficient and reliable system and method are provided for detecting tongue strength at both maximal and submaximal performance. In addition, fatigability and endurance tests may be conducted with facility.

SUMMARY OF THE INVENTION

In accordance with the present invention, a system and method for detecting pressure generated within a selected part of the body of a person is provided. The system includes a pressure sensor of a suitable size to fit within a selected part of the body, such as the person's mouth or hand, for sensing pressure generated by the selected part of the body. More specifically, the pressure sensor may take the form of a relatively pliable, fluid-filled bulb of a suitable size to fit within the mouth of a person to sense pressure generated within the mouth. The fluid-filled bulb is sufficiently resilient to deform under the pressure generated within the mouth in order to sense the pressure generated within the mouth and to thereafter return to original shape when the pressure generated within the mouth is removed. Likewise, a relatively pliable, fluid-filled bulb of a suitable size to fit within the hand of a person may be utilized in order to sense pressure generated by the squeezing of the hand.

A pressure transducer is removably connectable with the pressure sensor used for the hand or the mouth for converting the moment-to-moment pressure sensed by the pressure sensor to an electrical signal representing the sensed pressure. In order to permit pressure measurements of both the hand and the mouth, the transducer may be alternatively connected to the hand bulb and the mouth bulb.

For the purpose of detecting peak pressure, the system includes a peak-pressure detection circuit responsive to the electrical signal representing the sensed pressure which is output by the transducer. The peak-pressure detection circuit functions to detect the peak pressure sensed by the pressure sensor during a selected period of time. An output signal representing the peak pressure is produced by the peak-pressure detection circuit. A polarity selector is provided for the peak-pressure detection circuit to selectively enable the detection of both positive and negative peak pressures. A reset enables the peak-pressure circuit to be reset for subsequent tests.

A pressure comparator circuit is also responsive to the electrical signal representing the sensed pressure which is output by the transducer. The pressure comparator circuit functions to compare the sensed pressure from the pressure sensor to a predetermined pressure level to produce an output indicating the proportion of the sensed pressure relative to the predetermined pressure level. The output of the comparator circuit may then be compared to a selected level in order to ascertain the time period that such output can be sustained at or above the selected level. This procedure provides useful information on endurance and fatigability.

A pressure level adjustment is provided for the pressure comparator circuit to enable selective adjustment of the predetermined pressure level. If the predetermined pressure level is set at the peak pressure generated by a particular person, then the output of the comparator circuit reflects the proportion of the moment-to-moment pressure being generated by the person relative to the person's peak performance.

An output display is provided for selectively displaying the sensed moment-to-moment pressure, the peak pressure, and the output indicating the proportion of the sensed pressure relative to the predetermined pressure level. More specifically, the output display includes a first display for selectively displaying the sensed pressure, the peak pressure, and the selected predetermined pressure level. In addition, the output display includes a second display in the form of a bar graph display for displaying the proportion of the sensed pressure relative to the predetermined pressure level.

In addition to the pressure detection system, a method for analyzing pressure generated within at least one selected part of the body of a person is also provided. In accordance with such method, a pressure sensor of a suitable size is provided to fit within the mouth of a person. The pressure sensor is inserted within the person's mouth to sense the moment-to-moment pressure generated within the mouth.

The sensed pressure is then compared to a predetermined pressure level. An output representing the fractional proportion of the sensed pressure relative to the predetermined pressure level is produced. The fractional proportion is then compared to a selected level so that the period of time in which the person can sustain the fractional proportion at or above the selected level can be ascertained. The endurance or fatigability of the tongue is thereby measured in terms of the patient's ability to maintain a selected pressure for a measured amount of time.

The predetermined pressure level to which the sensed pressure is compared may be selectively adjusted. When the predetermined pressure level is selectively set to the peak pressure level of the individual person, the output representing the fractional proportion of the sensed pressure level relative to the predetermined pressure level reflects the moment-to-moment performance of the patient relative to the patient's maximal performance.

The method for analyzing pressure generated within the mouth of the person may be supplemented with an analysis of pressure generated by the hand of the person. For this purpose, a second pressure sensor is provided having a suitable size to fit within the hand of the person. The pressure sensor is inserted within the hand of the person in position to sense the moment-to-moment pressure generated on the pressure sensor when the hand is squeezed.

The sensed pressure from the hand is then compared to a predetermined pressure level for the hand. An output representing the fractional proportion of the sensed pressure from the hand relative to the predetermined pressure level for the hand is then produced. The period of time in which the fractional proportion for the hand is maintained at or above a selected level for the hand is then measured. When the predetermined pressure level for the hand is selectively adjusted to the peak pressure level for the hand of the particular individual, the output representing the fractional proportion of the sensed pressure from the hand relative to the predetermined pressure level for the hand reflects the moment-to-moment performance of the hand relative to the peak performance of the hand. Information on the endurance and fatigability of the person's hand is thereby provided.

BRIEF DESCRIPTION OF THE DRAWINGS

The foregoing summary, as well as the following detailed description of the preferred embodiments of the present invention, will be better understood when read in conjunction with the appended drawings, in which:

FIG. 2 is a schematic representation of the circuitry employed for producing a reference ground voltage for the circuitry of the device;

FIG. 3 is a schematic representation of the circuitry employed for producing a regulated voltage for the circuitry of the device;

FIG. 4 is a schematic representation of an LCD display and the associated analog-to-digital converter and driver circuitry for the LCD display of the device together with a low battery detection circuit employed in the device;

DETAILED DESCRIPTION OF THE PREFERRED EMBODIMENTS

Figure 1:
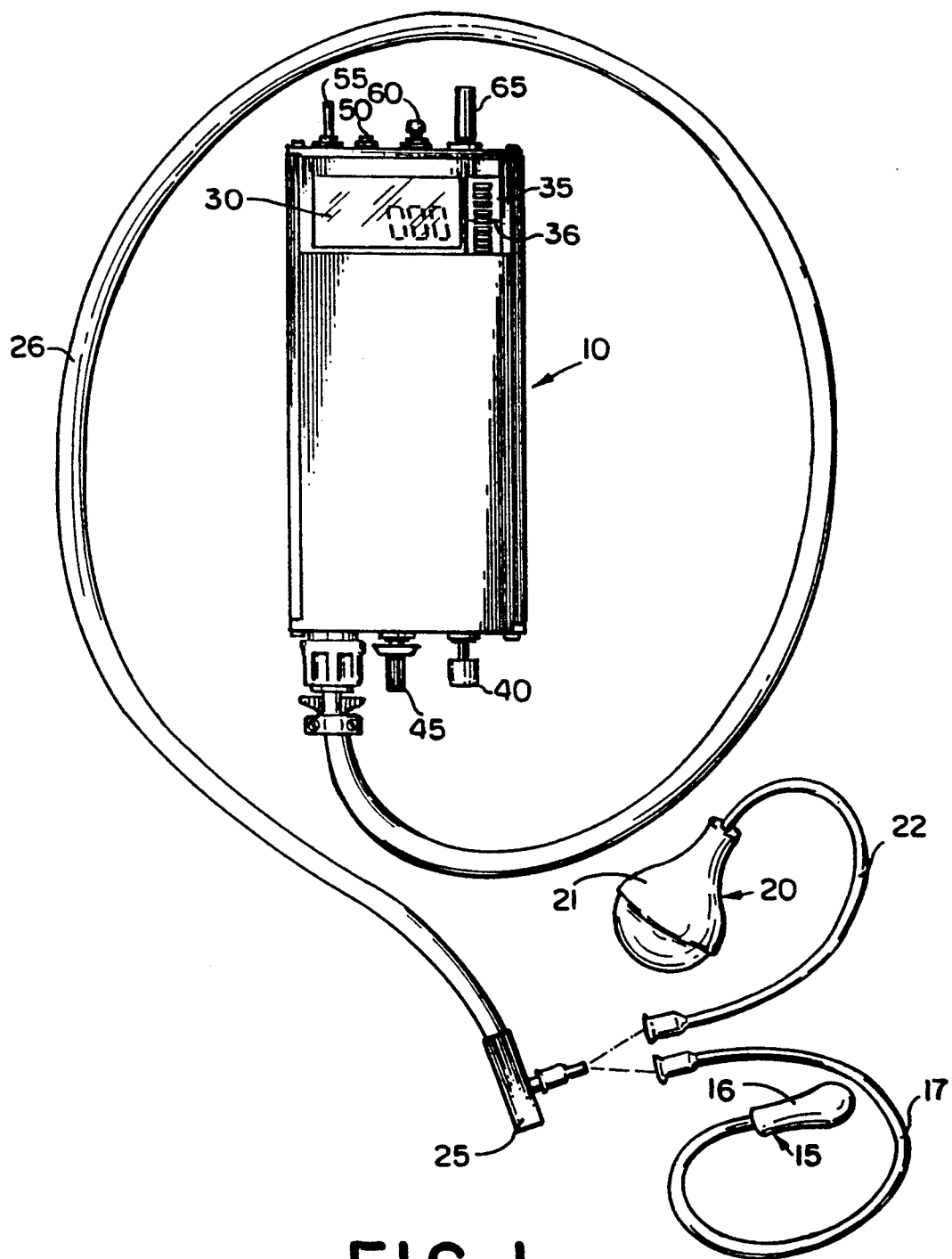
FIG. 1 is a front view of a portable device for monitoring and measuring pressure in accordance with a preferred embodiment of the present invention.

Referring to FIG. 1, a portable device, generally designated 10, is depicted for detecting and monitoring pressure generated within either the mouth or hand of a person. For the purpose of detecting pressure generated within the mouth of a person, the device 10 includes a pressure sensor unit 15 for use with the mouth. The pressure sensor unit 15 includes a generally pliable, fluid-filled bulb 16 of a suitable size to conveniently fit within the mouth of the person in order to sense pressure generated within the mouth. For this purpose, the bulb has sufficient resilience to deform under the pressure generated within the mouth and to thereafter return to original shape when the pressure generated by the mouth is removed. The bulb 16 provides an enclosed volume of fluid, such as water, which can be deformed from an original shape to accurately sense pressures generated within the mouth on the bulb 16. The mouth bulb 16 is sealed to a tube 17 which is removably connectable with a pressure transducer 25. The tube 17 is connected with an input port of the transducer 25 in a sealed manner so that the transducer can properly detect the amount of pressure exerted on the mouth bulb 16.

In order to measure pressure generated by the hand of a person, the device 10 also includes a pressure sensor unit 20 for use with the hand. The pressure sensor unit 20 includes a generally pliable, fluid-filled bulb 21 of a suitable size to fit within the hand of a person in order to sense pressure generated by the hand whenever the hand is squeezed. The hand bulb 21 has sufficient resilience to deform under the pressure generated by the hand and to thereafter return to an original shape when the pressure generated by the hand is removed. The hand bulb 21 provides an enclosed volume of fluid, such as water, for accurately sensing pressure generated by the hand through deformation of the shape of the hand bulb 21. The hand bulb 21 is sealed to tube 22 which functions to removably connect the hand bulb 21 in a sealed manner to the transducer 25.

The tongue bulb 16 may be in the form of a 1 ml latex rubber pipette bulb. Similarly, the hand bulb may take the form of a 10 ml bulb. Preferably, the bulbs are filled with a liquid such as water to provide increased resistance to compressability. Using relatively pliable hand and mouth bulbs to measure pressure eliminates the potential for shearing of sensitive tissue against a hard edge which may cause discomfort and thereby reduce a subject's ability, or at least willingness, to produce a maximal effort.

In operation, the pressure generated on the tongue bulb 16 by a person is supplied by tube 17 to the pressure transducer 25. The pressure exerted on the tongue bulb may be positive pressure whereby the tongue bulb 16 is compressed within the mouth by the pressure exerted by the tongue on the bulb 16 toward the roof of the mouth. Alternatively, negative pressure may also be supplied by expanding the bulb 16 within the mouth as a result of sucking pressure.

The pressure transducer 25 functions to convert the moment-to-moment pressure sensed by the mouth bulb 16 or the hand bulb 21 to an electrical signal representing the sensed pressure. The electrical signal is supplied to line 26 which electrically connects the pressure transducer 25 with the operational circuitry of the device 10. The electrical signal representing the pressure sensed by the bulb 16 or 21 is supplied as an electrical analog signal to the device.

In order to provide output information to the user, the device 10 includes an output display. As shown in FIG. 1, the output display includes a digital LCD display 30 for displaying 3 digits of information. In addition, the output display includes an LED display 35 which provides a bar graph display for the unit. The LED display 35 includes a stack of 9 visible LEDs. The middle LED is appropriately marked with level line 36 to provide a selected level of comparison for the user. In order to turn the device on and off, the device includes an on/off switch 40.

The device 10 may be selectively operated by the user in several different modes of operation. For this purpose, the device includes a rotary mode selection switch 45 to enable the user to select any of three different modes of operation. In one position of the selector switch 45, the device will operate in a "continuous pressure" mode of operation. In the "continuous pressure" mode of operation, the device functions to detect and display the moment-to-moment pressure being generated on the bulb 16 or 21. The moment-to-moment pressure sensed by the bulb 16 or 21 is indicated on the LCD display 30 as a calibrated unit of standard pressure. For example, the LCD display may function to display the pressure generated on the bulb 16 or 21 in units of kilopascals (kPa). In the "continuous pressure" mode, the indication of sensed pressure on the LCD display changes as the moment-to-moment pressure exerted on the bulb 16 or 21 changes. In order to provide a supplemental display on an oscilloscope, for example, the device also includes an external jack 50 which outputs an electrical signal representing the moment-to-moment pressure detected by the bulb 16 or 21.

When the selector switch 45 is changed to a second position, the device operates in a "peak hold" mode of operation. In the "peak hold" mode of operation, the peak pressure detected by the device during a particular run is held as a stored voltage within the device and displayed on the LCD display 30 as a calibrated unit of standard pressure, i.e., kPa. The peak pressure displayed on the LCD display 30 reflects the maximal pressure achieved by the subject during a particular run. For subsequent runs, the device must be reset. For this purpose, the device 10 includes a push-button reset switch 60 which functions to reset the peak pressure displayed on the LCD display 30 back to zero, or approximately zero, to enable the device to be used in a subsequent run for detecting peak pressure.

The device may be operated to detect both positive and negative peak pressures. A toggle-type polarity switch 55 on the device may be switched by the user between a positive setting which causes the device to function to detect positive peak pressure and a negative setting which causes the device to function to detect negative peak pressure.

When the mode selection switch 45 is set to a third position, the device functions in a "comparative pressure" mode of operation in which the device displays the proportion of the sensed moment-to-moment pressure from the bulb 16 or 21 relative to a predetermined pressure level. In this mode of operation, the LED display 35 is activated in order to provide the subject with feedback on the strength of the pressure response. The LED display 35 provides a bar graph of the proportion of the moment-to-moment pressure sensed by bulb 16 or 21 relative to the predetermined pressure level. In effect, the LED display 35 provides a convenient indication in bar graph form of the person's effort at generating pressure on the bulb 16 or 21 relative to the predetermined level.

A pressure level adjustment is provided to enable the user to selectively adjust the predetermined pressure level to which the sensed moment-to-moment pressure is compared. For this purpose, the device includes a pressure level adjustment knob 65 which may be rotated to selectively change the predetermined pressure level. In the "comparative pressure" mode of operation, the predetermined pressure level selected by the user via adjustment knob 65 is displayed as a calibrated amount of standard pressure, i.e., kpa, on the LCD display 30. Whenever pressure is exerted on the pressure bulb 16 or 21, the proportion of the sensed moment-to-moment pressure relative to the predetermined pressure level selected by adjustment knob 6 is displayed in bar graph format on the LED display 35.

In the "comparative pressure" mode of operation, the device is useful for fatigue tests and for observing the ability of a person to control a submaximal response. If the adjustment knob 65 is set so that the predetermined pressure level displayed on LCD display 30 corresponds to the peak pressure generated by the person on the bulb 16 or 21, the top LED in the LED display 35 becomes activated when the sensed moment-to-moment pressure on the bulb corresponds to the person's peak pressure performance. The marking line 36 located beside the middle LED in the stack of LEDs 35 is then used to represent 50% of the person's maximal level of pressure. In order to measure endurance or fatigability at the 50% maximal pressure level in the "comparative pressure" mode of operation, the person's effort at maintaining illumination of the LED display 35 at or above the 50% level as provided by marking line 36 is timed.

Figure 5:
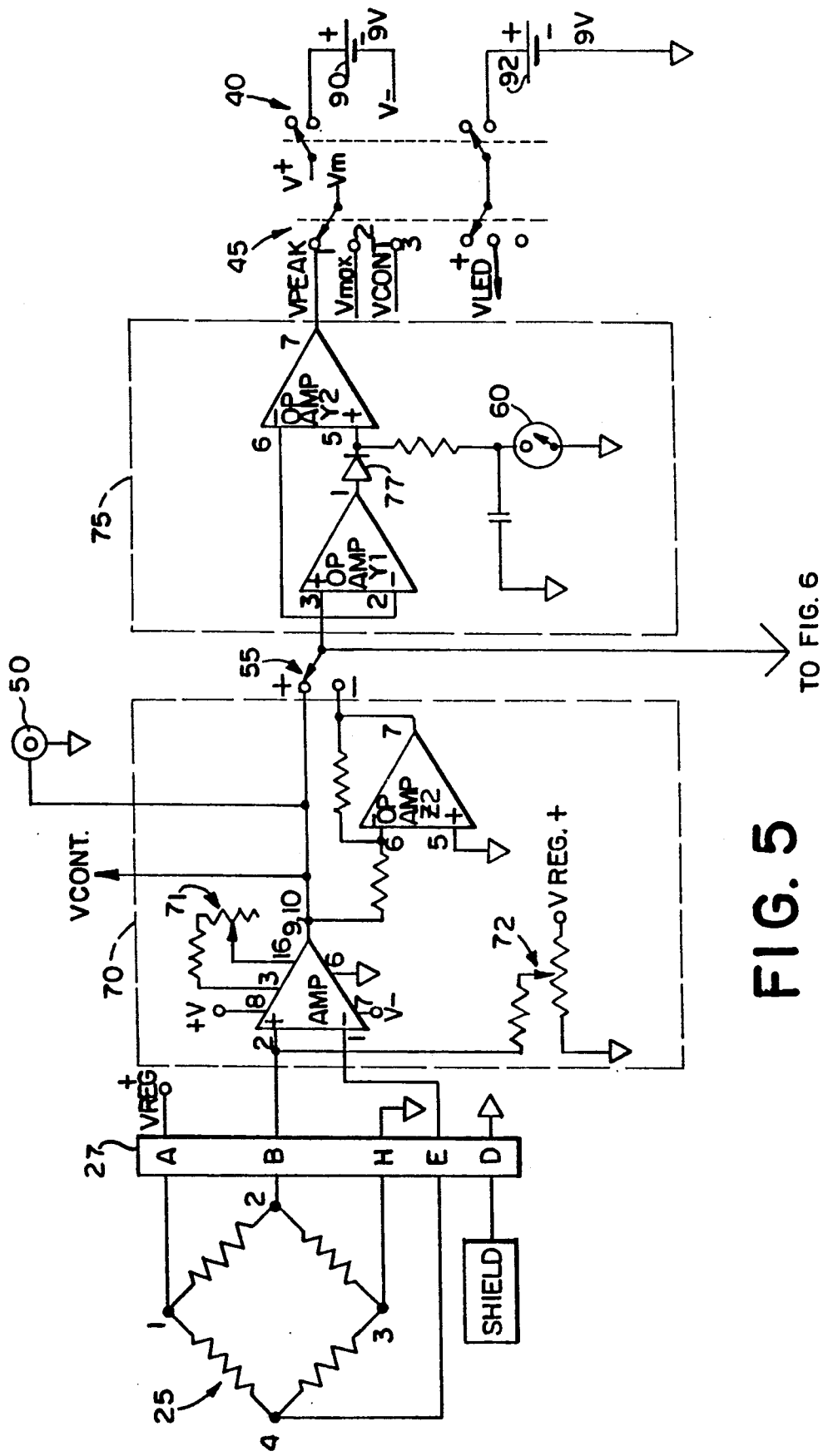
FIG. 5 is a schematic representation of the circuitry for the transducer, a signal amplifier, and a peak-pressure detection circuit employed in the device.
Figure 6:
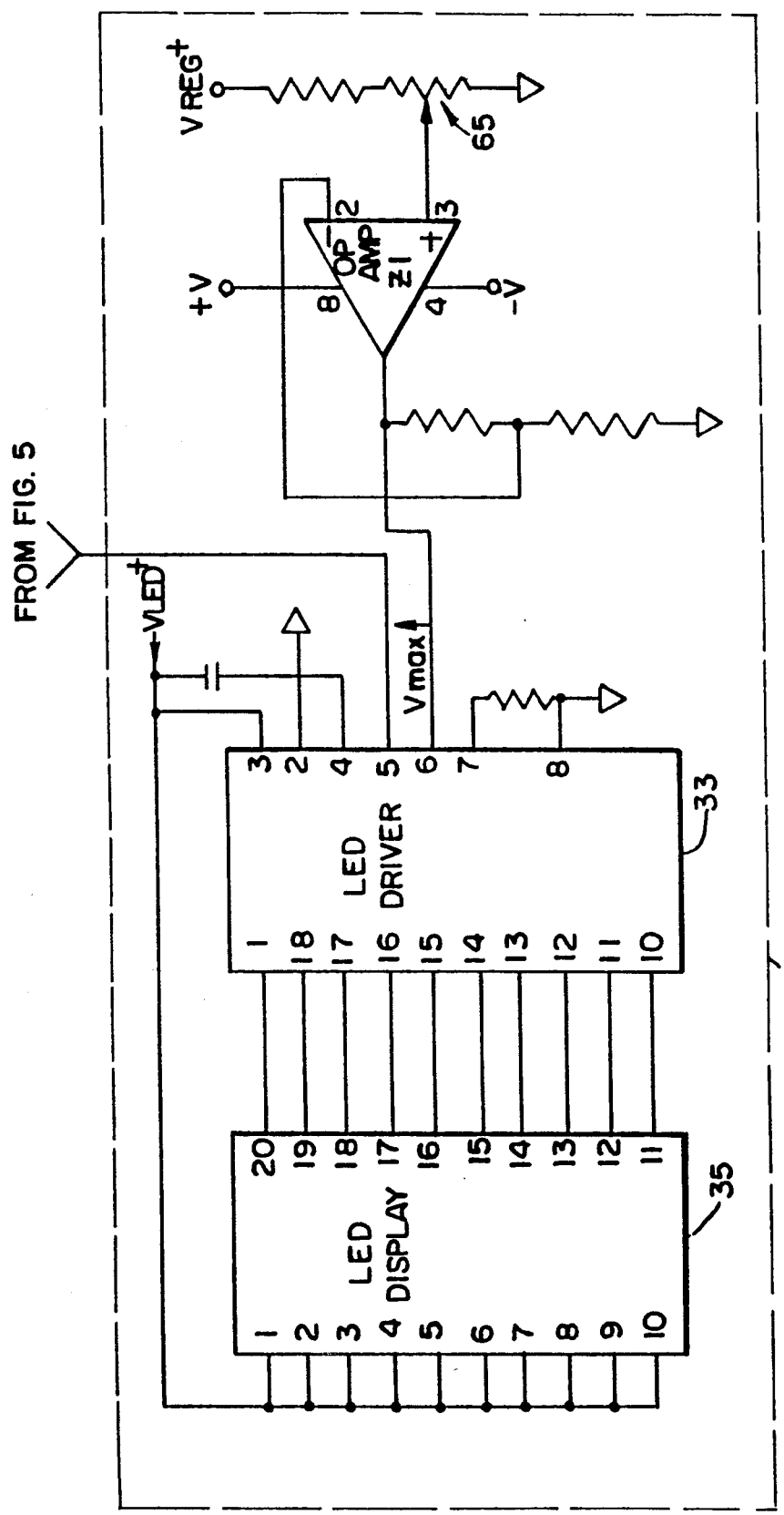
FIG. 6 is a schematic representation of an LED display and associated driver circuitry for the LED display employed in the device.

Referring to FIG. 5, the portable device 10 is powered by two separate 9-volt batteries 90 and 92. The batteries are switchably connected with the circuitry for the device by the on/off switch 40 schematically shown in FIG. 5. When on/off switch 40 is turned "on," battery 90 supplies voltages V+ and V− to the operational circuitry of the device 10. The second 9-volt battery 92 is connected with the circuitry for the LED display 35 when the on/off switch is turned "on" and the mode selector switch 45 is set in position 2, as shown in FIG. 5, for the "comparative pressure" mode of operation. When selection switch 45 is set in position 2 with the device turned "on," voltage VLED+ is supplied by battery 92 to the appropriate circuitry for the LED display 35 as shown in FIG. 6.

In addition to the batteries 90 and 92, the circuitry providing the power source for the device includes a relative ground circuit 97, as shown in FIG. 2, for producing a relative ground potential at the output of OP AMP X1. The relative ground potential provided at the output of OP AMP X1 is used as the relative ground potential for the operational circuitry of the device. As shown in FIG. 3, the power source circuitry for the device also includes a voltage regulator circuit 95 for providing a regulated voltage VREG+ at the output of OP AMP X2 for the operational circuitry of the device. VREG+ may be selected to be on the order of approximately 2.84 volts.

Referring to FIG. 5, the pressure transducer 25 is connected to the operational circuitry of the device through connector 27. An electrical shield is provided to prevent spurious signals from being transmitted from the pressure transducer 25 to the operational circuitry of the device.

The analog signal from the transducer 25 representing the moment-to-moment pressure sensed by the bulb 16 or 21 is supplied as an input to amplifier circuitry generally designated 70. The amplifier circuitry 70 includes a signal amplifier AMP which receives the analog signal from the transducer 25 as an input. An amplified analog signal VCONT representing the moment-to-moment pressure detected by the pressure transducer is supplied as an output from the amplifier AMP on pins 9 and 10. The amplified analog signal VCONT representing the continuous or moment-to-moment pressure sensed by the pressure sensor is supplied as an input to terminal 3 of selector switch 45. The amplified analog signal VCONT representing the moment-to-moment pressure sensed by the sensor bulb 16 or 21 is also supplied to external jack 50.

An internal gain adjustment 71 is provided for the amplifier AMP to enable the user, if necessary, to adjust the gain of the amplifier AMP. A pressure balance adjustment 72 is also provided for the amplifier AMP to enable the user, if necessary, to zero the LCD display 30 at atmospheric pressure in order to maintain proper calibration of the device.

In order to permit the detection of both positive and negative peak pressures, the device includes polarity switch 55 schematically shown in FIG. 5. The amplified analog signal VCONT representing the moment-to-moment pressure sensed by the pressure bulb 16 or 21 is supplied to the positive terminal of the polarity switch 55 to permit the detection of positive peak pressure. In order to permit the device to detect negative peak pressure, the output VCONT of the amplifier AMP is also supplied to an inverter circuit provided by OP AMP Z2. The OP AMP Z2 inverts the VCONT signal to provide a −VCONT signal. The output of OP AMP Z2 is supplied to the negative terminal of polarity switch 55.

In order to detect the peak pressure generated during a particular run, the amplified analog signal VCONT or −VCONT from polarity switch 55 is supplied as an input to peak-pressure detection circuitry, generally designated 75. As shown in FIG. 5, the peak-pressure detection circuitry 75 includes OP AMP Y1 and OP AMP Y2. A diode 77 is connected between the output terminal of OP AMP Y1 and the positive input terminal of OP AMP Y2. The reset switch 60, schematically shown in FIG. 5, is connected from the positive input terminal of OP AMP Y2 to virtual ground. The output at pin 7 of OP AMP Y2 provides an analog voltage signal VPEAK representing the peak pressure level generated on the pressure bulb during a particular run. After a particular run is completed, the reset switch 60 functions to clear the peak pressure signal from the peak-pressure detection circuitry to enable a subsequent run.

The VPEAK signal which is output from OP AMP Y2 is supplied to terminal 1 of the mode selection switch 45. As shown in FIG. 5, when the selection switch 45 is set to terminal 1 corresponding to the "peak hold" mode of operation, the analog voltage VPEAK representing the peak pressure detected by the pressure bulb is supplied as output voltage Vm from the selection switch. When the selection switch 45 is set in contact with terminal 3 corresponding to the "continuous pressure" mode of operation, the amplified analog voltage VCONT representing the moment-to-moment pressure detected by the pressure bulb 16 or 21 is supplied as output voltage Vm by selection switch 45. Finally, when selection switch 45 is set in contact with terminal 2 corresponding to the "comparative pressure" mode of operation, the analog voltage Vmax representing the voltage required to illuminate the top LED in the LED display 35 is output as analog voltage Vm by the selection switch 45.

Referring to FIG. 6, the signal Vmax is derived from the LED display circuitry generally designated 85. As shown, voltage VLED+ from 9-volt battery 92 is supplied to LED driver 33 and LED display 35. The amplified analog voltage signal VCONT or −VCONT representing the moment-to-moment pressure sensed by the pressure bulb 16 or 21 is supplied from the output of polarity switch 55, as shown in FIG. 5, to input pin 5 of the LED driver 33. The predetermined voltage level at which the top LED of the LED display 35 becomes illuminated is provided by the output analog signal Vmax from OP AMP Z1. As shown in FIG. 6, the input voltage at terminal 3 of OP AMP Z1 can be selectively varied by the pressure level adjustment knob 65 in order to selectively adjust the level of output signal Vmax from OP AMP Z1. The Vmax output signal is supplied by OP AMP Z1 to terminal 2 of the mode selection switch 45 as shown in FIG. 5. The Vmax output from OP AMP Z1 is also supplied as an input to pin 6 of LED driver 33.

The LED driver 33 functions to compare the moment-to-moment pressure detected by the sensor bulb 16 or 21 with the predetermined pressure level represented by signal Vmax. More specifically, the amplified analog signal representing the moment-to-moment pressure sensed by bulb 16 or 21, such as signal VCONT from the positive terminal of polarity switch 55 or the inverse signal −VCONT from the negative terminal of the polarity switch 55, is supplied as an input to pin 5 of the LED driver 33. The LED driver 33 serves as a pressure comparator circuit for comparing the amplified analog signal VCONT or −VCONT representing the moment-to-moment pressure received at input pin 5 with the signal Vmax received at input pin 6 which represents the predetermined voltage level at which the top LED of the LED display 35 becomes illuminated. The LED driver 33 is connected with the LED display 35 to selectively illuminate one of the 9 LEDs showing on the LED display as an output indication of the proportion of the sensed moment-to-moment pressure relative to the predetermined pressure level represented by Vmax. Adjustment knob 65 enables the predetermined pressure level represented by Vmax to be selectively varied. As shown in FIG. 5, the voltage VLED+ is only supplied to activate the LED driver and LED display when the on/off switch 40 is turned "on" and the mode selection switch 45 is set in contact with terminal 2 corresponding to the "comparative pressure" mode of operation.

The voltage Vm produced as the output from the mode selection switch 45, as shown in FIG. 5, serves to activate the LCD display 30. Referring to FIG. 4, operation of the LCD display 30 is controlled by LCD control circuitry generally designated 80. As shown in FIG. 4, the analog voltage Vm from the output of the mode selection switch 45 is supplied across a voltage divider 81 to produce an attenuated input voltage at pin 31 of a combination analog-to-digital conversion (ADC) and LCD driver circuit 82. The ADC/LCD driver circuit 82 functions to convert the analog signal Vm representing voltage VPEAK, Vmax, or VCONT depending on the position of the mode selection switch 45 to a digital signal for output to the LCD display 30. When the mode selection switch 45 is in contact with terminal 1 as shown in FIG. 5, the voltage VPEAK representing the peak pressure detected by the pressure bulb 16 or 21 is supplied as analog signal Vm to voltage divider 81 to provide an attenuated input signal representing the peak pressure to ADC/LCD driver 82 for output on the LED display 30. When the mode selection switch 45 is set in contact with terminal 2, the voltage Vmax representing the predetermined pressure level required for illuminating the top LED in LED display 35 is supplied as analog voltage Vm to the voltage divider 81 to provide an attenuated input to the ADC/LCD driver 82 so that the selected predetermined pressure level may be displayed on the LCD display 30. When the mode selection switch 45 is set in contact with terminal 3, the voltage VCONT representing the moment-to-moment pressure sensed by the pressure bulb 16 or 21 is supplied as analog voltage Vm to voltage divider 81 to provide an attenuated input signal to the ADC/LCD driver 82 for output on the LCD display 30.

The device 10 also includes a sensitivity adjustment circuit 84 connected with the ADC/LCD driver 82. The sensitivity adjustment 84 enables the user to adjust the sensitivity of the voltmeter circuitry provided by the ADC/LCD driver 82 and the LCD display 30.

As shown in FIG. 4, the device also includes a low battery detection circuit generally designated 100. The low battery detection circuitry 100 includes a comparator 101 which supplies a LO BAT output signal to an exclusive OR gate 102. Exclusive OR gate 102 also receives input signal BP from the line interconnecting output terminal 21 of ADC/LCD driver 82 with input pin 1 of LCD display 30. The output of the exclusive OR gate 102 is supplied to input pin 38 of LCD display 30. A TEST signal is supplied from the ADC/LCD driver 82 to the comparator 101 and the gate 102. Whenever the voltage level of the battery 90 drops below 7.7 volts, the output from the exclusive OR gate 102 causes the LCD display 30 to display a low battery output signal to the user.

In a selected mode of operation, the instrument is initially turned on using the on/off switch 40. The mode selection switch 45 is set in position for the "continuous pressure" mode of operation. Prior to connecting either the hand pressure sensor unit 20 or the mouth pressure sensor unit 15 to the transducer 25, the LCD display should indicate 000. If the device is not properly zeroed at atmospheric pressure, adjustment may be made to the device via the internal pressure balance adjustment 72. Once the device is properly zeroed, the tongue and hand bulbs may then be filled with water for alternate connection to the device 10. In order to promote sanitary testing procedures, the tongue bulb 16, with or without connecting tube 17, may be disposable in order to permit a fresh item to be used with each person. Alternatively, a separate sterile sheath may be used to enclose the tongue bulb 16 for use with each person.

When ready for use, the end of the tube 17 from the tongue sensor unit 15 is connected to the port connector of the pressure transducer 25. The tongue bulb 16 is then inserted within the person's mouth. The tongue bulb 16 thereby functions to sense pressure generated within the person's mouth by deforming in shape in response to generated pressures.

The mode selection switch 45 is then set to the "peak hold" function to provide peak pressure detection. The reset button 60 is depressed so that the LCD displays 000. The polarity switch 55 is set in the positive position. In this mode of operation, the maximum positive pressure exerted within the mouth will be displayed on LCD display 30.

The patient then presses the tongue against the bulb as hard as possible so that the peak pressure generated within the person's mouth is displayed on the LCD display 30. After the peak pressure is detected and displayed on LCD display 30, the reset button 60 is depressed to zero the meter for another run. After a selected number of runs, the maximal pressure generated within the person's mouth is determined.

Next, the maximal hand pressure generated by the person is obtained. For this purpose, the hand pressure sensor unit 20 is attached to the port of the transducer 25. The mode selection switch 45 is set to the "peak hold" position and the reset button 60 is depressed to zero the LCD display for a peak pressure detection run. The polarity switch 55 is set in the positive position.

The hand bulb 21 is then placed in the person's palm so that the device can sense the peak pressure generated by the person when the hand bulb 21 is squeezed. The peak pressure generated on the hand bulb 21 is displayed on LCD display 30. The display 30 can be zeroed by depressing the reset button 60 for subsequent runs. After a selected number of runs, the peak pressure is determined.

Following measurements of the peak pressure generated within the mouth and hand of the person, endurance tests can then be run for both the mouth and hand. In order to measure tongue endurance, the tongue pressure sensor unit 15 must be attached to the transducer 25. The mode selection switch 45 is then set to the "comparative pressure" mode of operation. When the mode selection switch 45 is set in the "comparative pressure" mode position, the LED display 35 becomes activated and the LCD display 30 functions to display the predetermined pressure level selected by pressure level adjustment knob 65. The pressure level adjustment knob 65 is then adjusted so that the peak pressure achieved by the person during the peak pressure detection tests is displayed on the LCD display 30. Setting the pressure level adjustment knob 65 to the peak pressure level attained by the person causes the top LED in the LED display 35 to illuminate whenever that peak pressure is again achieved by the person.

The tongue bulb 16 is then inserted within the person's mouth and the person is instructed to produce a selected pressure level on the tongue bulb such as 50% of the maximal pressure effort of the person. When 50% of the maximal pressure is generated, the middle LED illuminates as indicated by marker line 36 on the LED display 35. The person is then instructed to maintain the illumination of the LED display at the selected 50% level indicated by the marker line 36 for as long as possible. The time that the person maintains the LED display at the marker level 36 is then timed. Tongue fatigue at 50% maximal tongue effort is thereby measured.

Hand endurance measurements can then be taken. For this purpose, the hand pressure sensor 20 unit is attached to the transducer 25. The mode selection switch 45 is set for operation in the "comparative pressure" mode. Adjustment knob 65 is then set so that the maximal hand pressure generated by the person is displayed on the LCD display 30. The adjustment knob 65 provides the predetermined pressure level at which the top LED becomes illuminated in the LED display 35. The person is then instructed to squeeze the hand bulb 21 so that the LED display is illuminated at the 50% maximal effort line indicated by marker line 36. The time period that the person is able to maintain the illumination of the LED display at the marker line 36 is then measured. This time measurement provides an indication of hand endurance or fatigability at 50% maximal effort.

Of course, variations in the suggested testing procedure may be made. For example, adjustment knob 65 may be set so that the predetermined pressure level indicated on LCD display 30 is at 50% of the maximal effort. In this event, the top LED becomes illuminated when 50% of the maximal pressure effort is produced. For use in this manner, the person would be instructed to maintain sufficient pressure for as long as possible to keep the top LED illuminated rather than the LED marked by level line 36. Other variations are also possible. For example, negative pressures caused by sucking may also be analyzed.

From the foregoing description, it can be seen that the present invention provides a convenient method and system for measuring pressure generated within a person's mouth or hand. It should be recognized, however, by those skilled in the art, that changes or modifications may be made to the above-described embodiments without departing from the broad inventive concepts of the invention. It should be understood, therefore, that the present invention is not limited to the particular embodiments disclosed herein, but is intended to cover all modifications and changes which are within the scope and spirit of the appended claims.

What is claimed is:

1. A pressure detecting system comprising:
   (a) a pressure sensor of a suitable size to fit within a selected body part of a person for sensing pressure generated by the selected body part of the person;
   (b) a transducer connectable with the pressure sensor for converting the pressure sensed by the pressure sensor to an electrical signal representing the sensed pressure; and
   (c) a pressure comparator circuit responsive to the electrical signal for comparing the sensed pressure to a predetermined pressure level for producing an output indicating the proportion of the sensed pressure relative to the predetermined pressure level; and
   (d) an output display responsive to the output from the pressure comparator circuit for indicating the proportion of the sensed pressure relative to the predetermined pressure level so that changes in the proportion resulting from changes in the sensed pressure can be monitored.

2. The system in accordance with claim 1 including a pressure level adjustment for the pressure comparator circuit to enable selective adjustment of the predetermined pressure level.

3. The system in accordance with claim 2 wherein said output display includes a first display for displaying the predetermined pressure level selected at the pressure level adjustment and a second display for displaying the proportion of the sensed pressure relative to the predetermined pressure level.

4. The system in accordance with claim 3 wherein the first display includes a numeric display and wherein the second display includes a bar graph display.

5. The system in accordance with claim 1 including a peak-pressure detection circuit responsive to the electrical signal for detecting the peak pressure sensed by the sensor.

6. The system in accordance with claim 5 including a pressure level adjustment for the pressure comparator circuit to enable selective adjustment of the predetermined pressure level to the peak pressure detected.

7. The system in accordance with claim 5 wherein said output display includes a display for displaying the peak pressure detected by the peak-pressure detection circuit in a calibrated amount of standard pressure units.

8. The system in accordance with claim 5 including a selection switch for the output display for selectively enabling the sensed pressure, the peak pressure, and the proportion of the sensed pressure relative to the predetermined pressure level to be displayed on the output display.

9. The system in accordance with claim 8 wherein said output display includes a first display for displaying the predetermined pressure level and a second display for displaying the proportion of the sensed pressure relative to the predetermined pressure level and wherein the selection switch selectively enables the predetermined pressure level to be displayed on the first display while the proportion of the sensed pressure relative to the predetermined pressure level is simultaneously displayed on the second display.

10. The system in accordance with claim 5 including a polarity selector for the peak-pressure detection circuit to selectively enable the detection of positive and negative peak pressures.

11. The system in accordance with claim 1 wherein the pressure sensor includes a fluid-filled bulb of a suitable size to fit within the mouth of the person to sense pressure generated within the mouth, the bulb having suitable resilience to deform under the pressure generated by the mouth and to return to original shape when the pressure generated by the mouth is removed.

12. The system in accordance with claim 11 wherein the fluid-filled bulb is filled with a liquid.

13. The system in accordance with claim 11 wherein the pressure sensor includes a second fluid-filled bulb of a suitable size to fit within the hand of the person to sense pressure generated within the hand, the bulb having suitable resilience to deform under the pressure generated by the hand and to return to original shape when the pressure generated by the hand is removed.

14. The system in accordance with claim 1 wherein the pressure sensor includes a fluid-filled bulb of a suitable size to fit within the hand of the person to sense pressure generated within the hand, the bulb having suitable resilience to deform under the pressure generated by the hand and to return to original shape when the pressure generated by the hand is removed.

15. The system in accordance with claim 14 wherein the fluid-filled bulb is filled with a liquid.

16. A portable pressure detecting device comprising:
(a) a fluid-filled bulb of a suitable size to fit within the mouth of a person to sense pressure generated within the mouth, the bulb having suitable resilience to deform under the pressure generated by the mouth and to return to original shape when the pressure generated by the mouth is removed;
(b) a transducer connectable with the bulb for converting the pressure sensed by the bulb to an electrical signal representing the sensed pressure;
(c) a pressure comparator circuit responsive to the electrical signal for comparing the sensed pressure to a predetermined pressure level for producing an output indicating the proportion of the sensed pressure relative to the predetermined pressure level;
(d) a peak-pressure detection circuit responsive to the electrical signal for detecting a peak pressure level sensed by the bulb; and
(e) an output display responsive to the electrical signal from the transducer, the output from the pressure comparator circuit and the peak pressure level detected by the peak-pressure detection circuit for selectively displaying the sensed pressure, the peak pressure, and the proportion of the sensed pressure relative to the predetermined pressure level so that changes in the proportion resulting from changes in the sensed pressure can be monitored.

17. The device in accordance with claim 16 including a pressure level adjustment for the pressure comparator circuit to enable selective adjustment of the predetermined pressure level.

18. The device in accordance with claim 17 wherein the output display includes a first display for displaying the selected predetermined pressure level and a second display for displaying the proportion of the sensed pressure relative to the predetermined pressure level.

19. The device in accordance with claim 16 including a polarity selector for the peak-pressure detection circuit to selectively enable the detection of positive and negative peak pressures.

20. The device in accordance with claim 16 wherein the fluid-filled bulb is filled with a liquid.

21. The device in accordance with claim 16 including a second fluid-filled bulb of a suitable size to fit within the hand of the person to sense pressure generated within the hand, the second bulb having suitable resilience to deform under the pressure generated by the hand and to return to original shape when the pressure generated by the hand is removed.

22. The device in accordance with claim 21 wherein the second fluid-filled bulb is filled with a liquid.

23. The device in accordance with claim 16 wherein the electrical signal representing the sensed pressure is an analog signal and wherein the system includes an analog-to-digital converter for converting the analog signal to a digital signal and wherein said output display includes a digital display for displaying the digital signal as calibrated amount of the sensed pressure.

24. The device in accordance with claim 16 wherein the peak-pressure detection circuit produces an analog signal representing the peak pressure detected and wherein the system includes an analog-to-digital converter for converting the analog signal to a digital signal and wherein said output display includes a digital display for displaying the digital signal as a calibrated amount of peak pressure detected.

25. The system in accordance with claim 16 including a pressure level adjustment for the pressure comparator circuit to enable selective adjustment of the predetermined pressure level to the peak pressure level.

26. A method for analyzing pressure generated within at least one selected body part of a person comprising:
(a) providing a pressure sensor of a suitable size to fit within a mouth of the person;
(b) inserting the pressure sensor within the mouth;
(c) sensing the pressure generated within the mouth on the pressure sensor;
(d) comparing the sensed pressure to a predetermined pressure level;
(e) producing an output representing the fractional proportion of the sensed pressure relative to the predetermined pressure level;
(f) comparing the output representing the fractional proportion to a selected reference level; and
(g) timing the period in which the output representing the fractional proportion exceeds the selected reference level.

27. The method in accordance with claim 26 including displaying an indication of the fractional proportion of the sensed pressure relative to the predetermined pressure level.

28. The method in accordance with claim 26 including selectively adjusting the predetermined pressure level.

29. The method in accordance with claim 26 including detecting a peak pressure level sensed by the pressure sensor.

30. The method in accordance with claim 29 including selectively adjusting the predetermined pressure level to the peak pressure level.

31. The method in accordance with claim 30 including displaying an indication of the fractional proportion of the sensed pressure relative to the predetermined pressure level.

32. The method in accordance with claim 26 wherein the pressure sensor includes a fluid-filled bulb having a suitable size to fit within the mouth of the person, the bulb having suitable resilience to deform under pressure generated within the mouth and to return to original shape when the pressure generated by the mouth is removed.

33. The method in accordance with claim 32 wherein the fluid-filled bulb is filled with a liquid.

34. The method in accordance with claim 26 including:
  (a) providing a second pressure sensor of a suitable size to fit within a hand of the person;
  (b) inserting the second pressure sensor within the hand of the person;
  (c) sensing the pressure generated within the hand on the pressure sensor;
  (d) comparing the sensed pressure from the hand to a predetermined pressure level for the hand;
  (e) producing an output representing the fractional proportion of the sensed pressure from the hand relative to the predetermined pressure level for the hand;
  (f) comparing the output representing the fractional proportion for the hand to a selected reference level for the hand; and
  (g) timing the period in which the output representing the fractional proportion for the hand exceeds the selected reference level for the hand.

35. The method in accordance with claim 34 including selectively adjusting the predetermined pressure level for the hand.

36. The method in accordance with claim 34 including detecting a peak pressure level sensed by the pressure sensor for the hand.

37. The method in accordance with claim 36 including selectively adjusting the predetermined pressure level for the hand to the peak pressure level for the hand.

38. The method in accordance with claim 37 including displaying an indication of the fractional proportion of the sensed pressure from the hand relative to the predetermined pressure level for the hand.

39. The method in accordance with claim 34 wherein the pressure sensor for the hand includes a fluid-filled bulb having a suitable size to fit within the hand of the person, the bulb for the hand having suitable resilience to deform under pressure generated within the hand and to return to original shape when the pressure generated by the hand is removed.

40. The method in accordance with claim 39 wherein the fluid-filled bulb for the hand is filled with a liquid.

41. The method in accordance with claim 34 including displaying an indication of the fractional proportion of the sensed pressure from the hand relative to the predetermined pressure level for the hand.

* * * * *